United States Patent [19]
Arendt et al.

[11] Patent Number: 5,990,214
[45] Date of Patent: Nov. 23, 1999

[54] LIQUID GLYCOL BENZOATE COMPOSITIONS

[75] Inventors: William David Arendt, Libertyville; Thomas Joseph Bohnert, Palatine; Mark Stephen Holt, Barrington, all of Ill.

[73] Assignee: Velsicol Chemical Corporation, Rosemont, Ill.

[21] Appl. No.: 08/904,049

[22] Filed: Jul. 31, 1997

[51] Int. Cl.$^6$ .............................. C08K 5/00; C08K 5/10; C08L 21/00; C08G 63/10

[52] U.S. Cl. ..................... 524/296; 524/296; 524/287; 252/12

[58] Field of Search ................. 524/296; 252/12

[56] References Cited

U.S. PATENT DOCUMENTS

| | | | |
|---|---|---|---|
| 2,823,192 | 2/1958 | Elwell et al. | 260/31.4 |
| 4,444,933 | 4/1984 | Columbus et al. | 524/292 |
| 4,654,390 | 3/1987 | Siegel | 524/296 |
| 4,656,214 | 4/1987 | Wickson | 524/287 |
| 4,829,099 | 5/1989 | Fuller et al. | |
| 4,876,304 | 10/1989 | Mertz et al. | 524/314 |
| 5,132,390 | 7/1992 | Domszy et al. | |
| 5,284,906 | 2/1994 | Schulz et al. | |
| 5,284,907 | 2/1994 | Schulz et al. | |
| 5,364,956 | 11/1994 | Matsumoto | 560/89 |
| 5,459,116 | 10/1995 | Ro et al. | |
| 5,545,472 | 8/1996 | Koubek et al. | 428/261 |

FOREIGN PATENT DOCUMENTS

| | | |
|---|---|---|
| 1042929 | 11/1978 | Canada. |
| 0157426 | 4/1985 | European Pat. Off. |
| 0 244 107 A1 | 11/1987 | European Pat. Off. |
| 0 292 599 A1 | 11/1988 | European Pat. Off. |
| 55-133305 | 10/1980 | Japan. |
| 496574 | 12/1938 | United Kingdom. |
| 1321383 | 6/1972 | United Kingdom. |

OTHER PUBLICATIONS

Ans. 6 of 40—1995: 769895—Chang—JP94–94509 Abstract pp. 11–12.

Ans. 16 of 40—1991: 7501—Ghanem et al.—Macromol. Ec. Super. Phys. Chem. Ind. Paris, France—Polym. Commun. 31(10), 388–91 (English) 1990—Abstract pp. 34–35.

Ans. 31 of 40—1982:599061—Asah—JP 80–160102 Abstract pp. 87–88.

Ans. 37 of 40—1971:530479—Schaafsma NL 6919151 19710622—Abstract pp. 98 and 99.

Ans. 40 of 40—1969:38531—Feit—ZA 6800149–19680528 Abstract pp. 101–103.

PCT Publication WO 97/16481 Published May 9, 1997 Application No. PCT/US98/15939.

International Search Report in PCT/US98/15939, dated Dec. 4, 1998.

Research Disclosure No. 13914, Nov. 1975.

Research Disclosure No. 17943, Mar. 1979.

Translation, Balkov, et al. "Use of Methyl Benzoate for Plasticizer Production", Zhurnal Prikladnoi Khimii, vol. 51, No. 3, pp. 706–707, Mar. 1978.

Sadykh–Zahde, "Synthesis and use of diethylene glycol esters of benzoic and synthetic fatty acids as plasticizers" S.I. Ref.Zh.Khim, 1977, Abstract No. 6N159, (1976), (5), 53–8.

Z. Chen, et al. "Synthesis of Diethylene Glycol Dibenzoate Catalyzed with Solid Acid", Huaxue Shijie (1987), 28(I), 13–16 and (abstract).

*Primary Examiner*—David W. Wu
*Assistant Examiner*—T. Zalukaeva
*Attorney, Agent, or Firm*—Hugh A. Abrams; Sidley & Austin

[57] ABSTRACT

The present invention relates to liquid compositions comprising mixtures of esters derived from a) diethylene glycol and triethylene glycol and b) benzoic or toluic acid. The freezing point of the ester mixture is below the freezing points of the constituent esters when the relative concentrations of the constituent esters are within specified limits. The invention also relates oils and lubricants containing the present liquid ester compositions as plasticizing additives.

10 Claims, No Drawings

LIQUID GLYCOL BENZOATE COMPOSITIONS

FIELD OF THE INVENTION

This invention relates to liquid ester compositions. More particularly, this invention relates to mixtures of esters derived from certain aromatic monocarboxylic acids and specified combinations of oligomeric and optionally monomeric ethylene glycols. These mixtures are liquids at temperatures below the freezing point of the individual constituent esters.

DESCRIPTION OF THE PRIOR ART

Esters derived from 1) benzoic or toluic acid and 2) an aliphatic glycol or oligomer thereof together with methods for preparing these esters are described in the prior art.

Certain of these esters, particularly esters derived from glycols containing from 2 to about 9 carbon atoms, constitute a preferred class of plasticizers for polyvinyl chloride and other inherently rigid organic polymers because of the ability of the esters to improve the processability of the rigid polymers without adversely affecting their desirable physical properties.

U.S. Pat. No. 4,656,214, which issued to Wickson on Apr. 7, 1987 describes diesters of 1) linear glycols containing from 2 to 8 carbon atoms, 2) a first carboxylic acid of the formula $R^1R^2R^3C(O)OH$ and 3) a second carboxylic acid of the formula $R^5C(O)OH$, wherein $R^1$ and $R^2$ are individually selected from alkyl containing from 1 to 4 carbon atoms, $R^3$ is hydrogen or alkyl from 1 to 6 carbon atoms, $R^5$ is selected from the group consisting of phenyl, mono- di- and trialkyl-substituted phenyl containing from 9 to 12 carbon atoms and —$(CH_2)_n$Ph where Ph is phenyl and the value of n is from 1 to 6, inclusive. The esters contain from 16 to 19 carbon atoms and are useful as stain-resistant plasticizers for polyvinyl chloride.

The use as plasticizers of esters derived from benzoic acid and a polyhydric alcohol is described in Japanese Laid Open Patent Application No. 54/18859, published on Feb. 13, 1979.

Published European Patent Application No. 244,107, issued on Nov. 4, 1987 describes plasticizer compositions for elastomers comprising I) a trimellitate ester, II) a saturated linear dicarboxylate ester obtained by reacting 1) a dicarboxylic acid with at least one monohydric alcohol or 2) an aliphatic monocarboxylic acid with at least one of diethylene glycol, triethylene glycol and tetraethylene glycol, and III) a dialkyl ester of a thiodicarboxylic acid.

U.S. Pat. No. 4,444,933 to J. Anderson and P. Columbus describes cyanoacrylate adhesives containing a plasticizer that is selected from dipropylene glycol dibenzoate, diethylene glycol dibenzoate, a mixture of the foregoing two compounds, butylbenzyl phthalate, dibutyl phthalate or a benzoate ester of di-or polyhydroxy branched aliphatic compounds.

Research Disclosure No. 17943, published on Mar. 10, 1979 describes plasticized road marking compositions containing from 10 to 50 weight percent of a plasticizer described as a benzoic acid ester exemplified by glyceryl tribenzoate, neopenyl dibenzoate, triethyleneglycol dibenzoate and trimethylolethane tribenzoate or a polyester.

Esters derived from benzoic acid and either di- or triethylene glycol are particularly desirable because of the wider availability and lower cost of these glycols relative to the corresponding propylene glycols. One of the disadvantages of using benzoic or toluic acid esters of ethylene glycol, di- and triethylene glycol as plasticizers is that these esters are solids at 25°. Polymer compositions containing these esters as additives typically require heating to at least the melting point of the additive to uniformly blend the additive into the composition.

SUMMARY OF THE INVENTION

The present invention is based on the discovery that within a relatively limited range of proportions blends containing the di- and triethylene glycol esters of benzoic and toluic (methylbenzoic) acids are liquids below the freezing point of the individual constituent esters.

When the present blends are used as plasticizers they can optionally include at least one additional ester that is a liquid at 25° C. and is conventionally used as a plasticizer for organic polymers. The additional liquid ester(s) increases the relative concentration of triethylene glycol ester relative to diethylene glycol ester that can be present in a composition that is liquid below the freezing points of both glycol esters.

DETAILED DESCRIPTION OF THE INVENTION

This invention provides liquid ester compositions comprising:

1) a first diester of the formula $ArC(O)(OCH_2CH_2)_2O(O)CAr$ and
2) a second diester of the formula $ArC(O)(OCH_2CH_2)_3O(O)CAr$;

wherein Ar represents a phenyl or methylphenyl radical, and the freezing point of said compositions are below the freezing points said first and second diesters.

The weight ratio of said first diester to said second diester is preferably from 1.22:1 to 9:1.

In preferred embodiments the first and second diesters preferably constitute at least 50 weight percent of the present liquid ester composition. The remaining ingredients of these preferred embodiments are esters exhibiting freezing points below 25° C. These additional esters are derived from mono- or polyhydric alcohols and aromatic or aliphatic mono- and/or dicarboxylic acids. The presence of these additional liquid esters increases the concentration of the triethylene glycol diester relative to the diethylene glycol diester that can be present in compositions that are liquid below the freezing point of these glycol diesters.

Examples of the additional liquid esters that can be present in the ester compositions or the present invention include but are not limited to 1) diesters derived from benzoic acid and diols containing from 3 to 10 carbon atoms, 2) esters derived from benzoic acid and monohydric alcohols containing from 8 to 12 carbon atoms, 3) aliphatic esters of the formula $R^1O(O)C(CH_2)_mC(O)OR^1$, and 4) esters derived from phthalic acid and alcohols containing from 4 to 12 carbon atoms. In the preceding formula $R^1$ is an alkyl individually selected from the group consisting of alkyl and aryl radicals containing from 4 to 12 carbon atoms, and m represents an integer from 2 to 8. The combined weight of these additional plasticizers can constitute up to 50, and preferably from 10 to 35 weight percent of the present liquid ester composition. It will be understood that suitable diols can contain hetero atoms such as oxygen in the hydrocarbon chain.

Specific examples of additional liquid esters that can be present in the ester compositions of the present invention include but are not limited to propylene glycol and dipropylene glycol dibenzoates, neopentyl glycol dibenzoate, dialkyl adipates, glutarates, azelates and sebacates, isodecyl benzoate and butyl benzyl phthalate.

The additional liquid esters described in the preceding paragraphs can constitute up to 50 weight percent of the present liquid ester compositions. The presence of these optional liquid esters reduce to about 0.5:1 the weight ratio of the present diethylene glycol benzoate or toluate to triethylene glycol benzoate or toluate required to yield a liquid ester composition at 28° C.

The present invention also provides compositions comprising 1) an organic polymer such as polyvinyl chloride and 2) up to about 60 weight percent of the present liquid ester compositions as plasticizers. The ester compositions can also be included as plasticizing additives in liquid compositions such as oils and lubricants.

The novelty of the present ester compositions resides in the lower freezing point of the compositions relative to the freezing temperatures of the two required diesters that constitute at least 50 percent by weight of these compositions. For example, diethylene glycol dibenzoate freezes from 28–29° C., and triethylene glycol dibenzoate freezes from 46–48° C. Unexpectedly, all of the present ester compositions are liquids below 28° C. The actual freezing point of any specific ester composition will be determined by the relative concentrations of the constituent esters.

The Aromatic Carboxylic Acid

Aromatic carboxylic acids suitable for preparing the present liquid ester compositions can be represented by the general formula ArC(O)OH, wherein Ar represents a phenyl or methylphenyl radical. The class of carboxylic acids includes benzoic acid and the isomeric toluic acids. It will be understood by those skilled in the art that the corresponding anhydrides and acyl halides can be used in places of the carboxylic acids.

The Glycol Mixture

The alcohol portions of the solid esters of the present compositions are derived from diethylene glycol and triethylene glycol.

The relative concentrations of the esters derived from each of the two required oligomeric ethylene glycols used to prepare the present compositions is critical to obtaining compositions that are liquid below 28° C. The ester derived from diethylene glycol constitutes from 55 to 90 weight percent, preferably from 55 to 65 weight percent of the mixture of esters derived from di- and triethylene glycol.

The present ester compositions can be obtained by first preparing each of the esters individually using any of the known methods for preparing this class of compounds. Following purification the esters are melted prior to or after being combined in the desired proportions.

In accordance with a preferred method, the present ester compositions are prepared in situ by reacting benzoic acid or one of the isomeric toluic acids with a mixture of diethylene glycol and triethylene glycol. The relative concentration of each glycol is calculated to yield an ester composition within the scope of the present invention, assuming that substantially all of the glycols react with the acid.

Other glycols such as ethylene glycol, propylene glycol and dipropylene glycol can be included in the mixture of glycols used to prepare the present ester compositions, so long as the presence of these additional glycols does not detract from the objectives of the present invention.

Reaction conditions and apparatus required to prepare esters from the corresponding carboxylic acid(s) and mono- or polyhydric alcohol(s) are sufficiently well described in the prior art that a detailed description in the present specification is not required. As taught hereinbefore, the corresponding acyl halides or anhydrides can be used in place of the acid. Reactions using these alternative reactants are described in the prior art.

To accelerate formation of the present ester compositions, the reaction mixture containing the benzoic or toluic acid and mixture of glycols is preferably heated to the boiling point while the water formed as a by-product is continuously removed by distillation from the reaction mixture. Catalysts such as mineral acids and alkyl titanates can be present in the reaction mixture, and a low boiling hydrocarbon such as hexane can be present in the reaction mixture to facilitate removal of the water.

The esters can be purified by neutralization of and acid catalysts and/or removal of volatile impurities under reduced pressure.

Use of the Present Liquid Ester Compositions as Plasticizers for Organic Polymers The liquid ester compositions of the present invention are particularly useful as plasticizers to improve the processability and physical properties of both rigid and non-rigid organic polymers.

Polymers preferred for use with the present ester composition include polyvinyl chloride and copolymers derived from vinyl chloride and at least one additional copolymerizable mono- or diolefinically unsaturated compounds, including but not limited to vinylidene chloride, vinyl esters of carboxylic acids such as vinyl acetate, and vinyl propionate, esters of ethylenically unsaturated acids such as the alkyl acrylates and -methacrylates. Preferably at least 70 percent of the repeating units of these copolymers are derived from vinyl chloride.

When used as plasticizers, the present ester compositions can be used alone or in combination with one or more plasticizers known to those skilled in the art to achieve a desired combination of processability and properties in the final polymer composition.

The concentration of plasticizer(s) in any given polymer composition can vary widely, based on the desired properties and intended use of the composition. Concentrations of from 1 to 200 parts of plasticizer per hundred parts by weight of resin (phr) have been reported, however this range is preferably from 10 to 100 phr.

The types of polymer compositions into which the present liquid ester compositions can be advantageously incorporated as additives include but are not limited to vinyl flooring laminates, latex caulks, adhesives, coating compositions that are applied as liquids or finely divided solids, and inks.

The ester compositions of this invention are also useful as seal-swelling additives for oils and lubricants.

The preparation and use of the liquid ester compositions of this invention are described in detail in the following examples, which should not be interpreted as limiting the scope of the invention described in the accompanying claims.

EXAMPLE 1

Ester compositions were prepared by combining in glass containers solid diethylene glycol benzoate (DEGB) and triethylene glycol benzoate (TEGB) in the proportions listed in Table 1. Each of the resultant mixtures weighed ten grams and was heated in an oven maintained at a temperature of 80° C. for a period of time sufficient to form a liquid. Each of the liquid compositions was then placed for 24 hours in a freezer maintained at a temperature of −12° C. After 24 hours the containers were examined for evidence of crystallization. The compositions of each sample and the results of the examination are recorded in Table 1.

TABLE 1

| Weight Percent | | |
|---|---|---|
| DEGDB | TEGDB | Physical State at −12° C. |
| 100 | 0 | Solid (c) |
| 0 | 100 | Solid (c) |
| 75 | 25 | Liquid |
| 65 | 35 | Liquid |
| 55 | 45 | Liquid |
| 90 | 10 | Liquid | c = Comparative Example

EXAMPLE 2

Polyvinyl Chloride Resilient Flooring

This example demonstrates the use of the present ester compositions as plasticizers for resilient flooring applications. Resilient flooring generally consists of at least layers of a vinyl polymer plastisol on a dimensionally stable substrate. The plastisol used as the top layer is clear and provides wear resistance. The next layer is a vinyl foam prepared using a plastisol containing a chemical blowing agent. Plasticizers that are used are selected for this application are required to be effective, stable, provide stain resistance and processability.

A blend of diethylene glycol dibenzoate, triethylene glycol dibenzoate and di-2-ethylhexyl adipate in the weight ratio of 1.0 to 0.55 to 0.27, referred to below as blend A, was tested in resilient flooring laminates.

Tables 2 to 4 list the formulations evaluated. The formulations were prepared by mixing the ingredients on a low speed, high intensity mixer and degassing. The foam layer was coated onto a ceramic felt backing and gelled at 130° C. for one minute in a Mathus oven. The top layer was then applied and the construct was fused at 190° C. for one and a half minutes. Tables 4 to 8 list the property data obtained from the constructs prepared.

TABLE 2

Top Coat Formulation

| Ingredient | Identification | Manufacturer | Parts By Weight |
|---|---|---|---|
| GEON 173 | PVC Dispersion Resin | GEON | 100 |
| Plasticizer | Blend A | Present Invention | 36 |
| Diluent Plasticizer | Isodecyl benzoate | Velsicol | 12 |
| PEG 400 Monolaurate | Polyethylene glycol 400 molecular weight monolaurate | Stepan | 1.4 |
| Therm-Chek 1776 | Mixed metal stabilizer | Ferro | 3.0 |
| Stabilizer | Epoxidized soy bean oil | Velsicol | 2.0 |

TABLE 3

Foam Layer Formulation

| Ingredient | Identification | Manufacture | Parts By Weight |
|---|---|---|---|
| GEON 121 A | PVC dispersion resin | GEON | 68.8 |
| GEON 217 | PVC blending resin | GEON | 31.2 |
| Plasticizer | Blend A | — | 24.3 |
| Diluent Plasticizer | Isodecyl benzoate | Velsicol | 19.4 |
| AZO Dispersion (Table 3) | Azodicarbonamide dispersion | — | 12.8 |
| PEG 400 Monolaurate | Polyethylene glycol 400 molecular weight monolaurate | Stepan | 1.5 |
| Atomite | Calcium Carbonate | E.C.C. | 14.8 |

TABLE 4

AZO Dispersion Formulation For Use in Table 3

| Ingredient | Identification | Manufacturer | Parts By Weight |
|---|---|---|---|
| Plasticizer | Blend A | — | 36.4 |
| Diluent Plasticizer | Isodecyl benzoate | Velsicol | 12 |
| PEG 400 Monolaurate | Polyethylene Glycol 400 molecular weight monolaurate | Stepan | 1.0 |
| CELLOGEN AZ, 3990, azodicarbonamide | Blowing agent | Uniroyal Chemical | 13.2 |
| Asaco AZO 77S, Zinc Oxide | Activator | Asaco | 3.2 |
| TiPure R-900 $TiO_2$ | Pigment | Dupont | 26 |

TABLE 5

Resilient Flooring Screen Data
Top Coat Plastisol

Test Parameter
Brookfield RVT Low Shear Viscosity, 23° C., ASTM D-1824

Initial and 2 hours, Pa · s

| | |
|---|---|
| 2.5 RPM | 5.3 |
| 20 RPM | 3.7 |

24 Hours, Pa · s

| | |
|---|---|
| 2.5 RPM | 6.5 |
| 20 RPM | 4.5 |

3 Days, Pa · s

| | |
|---|---|
| 2.5 RPM | 9.6 |
| 20 RPM | 6.2 |

Ratios of 3 Day/Initial Viscosity

| | |
|---|---|
| 2.5 RPM | 1.8 |
| 20 RPM | 1.7 |

TABLE 5-continued

Resilient Flooring Screen Data
Top Coat Plastisol

High Shear Viscosity, Pa · s, ASTM D-1823, 23° C., @

| | |
|---|---|
| 10 psi | 5.2 |
| 40 psi | 12.6 |
| 70 psi | 17.6 |
| 100 psi | 20.7 |

TABLE 6

Resilient Flooring Screen Data
Foam Layer Plastisol

Test Parameter
Brookfield RVT Low Shear Viscosity, 23° C., ASTM D-1824

| | |
|---|---|
| Initial and 2 hours, Pa · s | |
| 2.5 RPM | 8.8 |
| 20 RPM | 5.4 |
| 24 Hours, Pa · s | |
| 2.5 RPM | 9.8 |
| 20 RPM | 5.8 |
| 3 Days, Pa · s | |
| 2.5 RPM | 16.3 |
| 20 RPM | 7.1 |
| Ratio of 3 Day/Initial viscosity | |
| 2.5 RPM | 1.9 |
| 20 RPM | 1.3 |
| High Shear Viscosity, Pa · s, 23° C., ASTM D-1823 | |
| 10 Psi | 4.9 |
| 40 psi | 10.5 |
| 70 psi | 13.8 |
| 100 psi | 15.3 |
| Foam Blow Ratio (Final thickness to initial thickness prior to fusion) | 3.8/1 |
| Foam Blown quality, visual assessment | Fair |

TABLE 7

Resilient Flooring Screen Data Construct
Top Over Foam

Test Parameter
Stain Resistance, Visual and instrumental reading

| | |
|---|---|
| Oil Brown Dye, 1% Sln | 5 |
| (0 = best and 10 = worst) | |
| Initial Rating, Δ E | 9.9 |
| Aged @ 70° C. | |
| 1 Week, ΔE | 4(8.5) |
| 2 Weeks, ΔE | 5(7.4) |
| 3 Weeks, ΔE | 3(5.8) |
| 4 Weeks, ΔE | 2(3.6) |
| Brown Polish, (B) | 6(55.2) |
| Mustard | 0 |
| Black Marker, (ΔE) | 6(25) |
| Vinyl Heat Stability, 200° C., visual estimate to total discoloration, % | |
| Rating after 2.5 min. | 5 |
| Rating after 5 min | 15 |
| Rating after 7.5 min. | 30 |
| Rating after 10 min. | 60 |
| Rating after 12.5 min. | 100 |

TABLE 8

Resilient Flooring Screen Data
Laminate (Top Over Foam)

Test Parameter

| | |
|---|---|
| Heat Resist., 70° C., Int. Δ E | 12.2 |
| Against standard white plate) | |
| Δ E, 1 week | 25.8 |
| Δ E, 2 week | 30.9 |
| Δ E, 3 week | 33.9 |
| UV Light Resistance (Atlas UV chamber) | |
| Δ E after, Initial | 18.3 |
| (Against standard white plate) | |
| 100 hours | 12.2 |
| 200 Hours | 12.3 |
| 300 Hours | 11.5 |
| 400 Hours | 15.2 |
| 500 Hours | 17.0 |

The data in the preceding tables demonstrate that blend A is an effective plasticizer for resilient flooring applications.

EXAMPLE 3

This example demonstrates the utility of the present liquid ester compositions in compositions intended for use as latex caulk. This type of caulk is used to seal cracks and fill gaps in new and existing residential and commercial buildings. A caulk consists basically of a polymeric binder and fillers. Compatible plasticizers are used in caulks to increase polymer solids and flexibility, improve adhesion and low temperature performance without adversely affecting storage stability or application properties of the formulation. A liquid ester composition of the present invention containing diethylene glycol dibenzoate, triethylene glycol dibenzoate and dipropylene glycol dibenzoate in the weight ratio of 1:0.5:0.5, referred to hereinafter as blend B, was incorporated into a latex caulk formulation to determine the utility of the present ester compositions for this application.

To function effectively a plasticizer must be compatible with the base polymer. To determine the compatibility of blend B with a convention caulk polymer, a blend of a caulk polymer emulsion and blend B was prepared using the types and amounts of ingredients listed in Table 9.

A compatible plasticizer should increase the viscosity of the emulsion. Data in Table 10 demonstrate that blend B increased the viscosity of the base emulsion. To further evaluate the compatibility of blend B with the caulk polymer, a 0.006 inch-thick film of the caulk formulation was applied to a glass plate using a draw down bar and allowed to dry for twenty four hours. The data in Table 11 demonstrate that the film was clear and tacky, which is indicative of compatibility between the caulk formulation and the plasticizer.

Blend B was incorporated into a typical latex caulk formulation. The ingredients listed in Table 12 were mixed in a low speed, high intensity mixer. The stability, adhesions, tensile strength and hardness of the caulk formulation were determined, and the data summarized in Tables 13 and 14. These data demonstrate that Blend B, a liquid ester composition of the present invention, functions well as a plasticizer for latex caulks.

TABLE 9

Caulk Polymer/Plasticizer Compatibility Data: Formulation

| Ingredient | Parts by Weight, Wet | Parts by Weight, Dry |
|---|---|---|
| Caulk Emulsion | 100 | 100 |
| Triton X-405 | 27.5 | 50.1 |
| Blend B (plasticizer) | 1.7 | 3.1 |

TABLE 10

Compatibility Data of Blend B With Rhoplex(R) 1785
Compatibility

| @ RT Storage | |
|---|---|
| Initial 1 Day | |
| Appearance | Clear |
| Tack | High |
| 7 Day | |
| Appearance | Clear |
| Tack | High |
| 28 Day | |
| Appearance | Clear |
| Tack | High |
| @ 50° C. Storage | |
| 1 Day | |
| Appearance | Clear |
| Tack | High |
| 7 Day | |
| Appearance | Clear |
| Tack | High |
| 28 Day | |
| Appearance | Clear |
| Tack | High |

Note:
The plasticizer was incorporated into the base emulsion at a level of 27.5 parts into 100 parts of the wet emulsion with 1.65 parts of Triton X-405. The plasticizer is at a level of 50% on the resin solids.

Note: The plasticizer was incorporated into the base emulsion at a level of 27.5 parts into 100 parts of the wet emulsion with 1.65 parts of Triton X-405. The plasticizer is at a level of 50% on the resin solids.

TABLE 11

Caulk Emulsion Viscosity Response Data: Rhoplex 1785
Brookfield RVT
Viscosities, RT, Pa · s

| Initial | |
|---|---|
| 2.5 RPM | 20 |
| 20 RPM | 7 |
| One Hour | |
| 2.5 RPM | 26 |
| 20 RPM | 8 |
| Two Hours | |
| 2.5 RPM | 29 |
| 20 RPM | 8 |
| 24 Hours | |
| 2.5 RPM | 44 |
| 20 RPM | 12 |
| 3 Days | |
| 2.5 RPM | 34 |
| 20 RPM | 10 |

Note:
Viscosity of neat emulsion is 0.6 Pa · s @ 2.5 RPM and 0.3 Pa · s @ 20 RPM. With the X-405 it is 1 Pa · s @ 2.5 RPM and 3 Pa · s @ 20 RPM's.

Note: Viscosity of neat emulsion is 0.6 Pa.s @ 2.5 RPM and 0.3 Pa.s @ 20 RPM. With the X-405 it is 1 Pa.s @ 2.5 RPM and 3 Pa.s @ 20 RPM's.

TABLE 12

Latex Caulk Formulation

| Raw Material | Manufacturer | Pounds | Gallons |
|---|---|---|---|
| RHOPLEX 1785 | Rohm & Haas | 417.2 | 46.73 |
| Water | | 26.9 | 3.23 |
| Triton X-405 | Rohm & Haas | 9.2 | 1 |
| Ethylene Glycol | Union Carbide | 12.5 | 1.35 |
| Tamol 850 | Rohm & Haas | 1.2 | 0.12 |
| Thickener, Natrosol(R) 250 MXR | Hercules | 1 | 0.09 |
| Dispersant, KTPP | Calgon | 1 | 0.05 |
| Blend B | Present Invention | 114.7 | 13.82 |
| Mineral Spirits, Varsol(R) #1 | Exxon | 20 | 3.05 |
| Adhesion Promoter, Silane Z-6040 | Dow Corning | 0.57 | 0.06 |
| Extender, Calcium Carbonate, Drikilite(R) | E.C.C. | 735 | 32.6 |
| Pigment, Titanium Dioxide, TiPure R-901 | Dupont | 10 | 0.3 |
| Ammonium Hydroxide, 28% | Fisher | 3.5 | 0.39 |
| Total | | 1352.77 | 102.79 |

Note:
Rohm & Haas formulation AS-85-1 used.

Note: Rohm & Haas formulation AS-85-1 used.

TABLE 13

Caulk Package Stability and Viscosity Data

| Test Parameter Initial Viscosity, Brookfield HAT, Helipath, RT, Pa · s | |
|---|---|
| 1 Day | 2300 |
| 7 Day | 2700 |
| Gunability, ASTM C-731 | |
| 1 Day, g/sec, RT | 6.7 |
| 7 Day, g/sec., RT | 5.5 |
| 28 Day, g/sec, RT | 2.4 |
| After 28 Days at 50° C. | 2.6 |
| After 5 cycles F/T | 3.1 |

TABLE 14

Physical Properties of Caulk

| Property | |
|---|---|
| Low Temp. Flex., 1" mandrel | |
| @ −24° C. | Pass |
| Shore A, 3 Week @ RT | |
| Initial, 1 sec | 23 |
| 10 sec. | 13 |
| Tensile, ASTM D-638 | |
| Maximum stress, psi | 43, (1) |
| Elongation, % | 680 |
| 180° Peel Adhesion, U.S. 230 Specification test | |
| Aluminum | |
| Lb/linear inch | 6.5, (1.6) |
| Failure mode | CP/C |
| Wood, Ponderosa Pine | |
| Lb/linear inch | 10.1 (2.4) |
| Failure mode | A/C |
| Wood Channel Crack | None |
| Tack Free Time, min. | 9 |
| Completion of Cure, days | 7 |

EXAMPLE 4

Latex Adhesive Applications

A latex adhesive is used to adhere a porous substrate to another porous or a non porous substrate. Latex adhesives are used in a large variety of applications from paper and paperboard packaging to use to glue wood furniture. A latex adhesive may consist of only a polymeric binder, but in most instances other polymer modifiers are used to formulate an adhesive for a specific purpose. In most instances a plasticizer is used to formulate an adhesive based on homopolymers such as polyvinyl acetate, but are just as often are used to modify copolymer-based adhesives. An effective, compatible plasticizer is used in a latex adhesive to thicken the base emulsion (viscosity response), to increase flexibility, to reduce glass transition temperature, improve adhesions and low temperature performance, extend open time, shorten set time and reduce heat seal temperature. A blend of diethylene glycol dibenzoate, triethylene glycol dibenzoate and dipropylene glycol dibenzoate in the weight ratio of 1 to 0.5 to 0.5 (blend C) was incorporated in latex adhesive formulations based on both homopolymer and copolymer emulsions to assess the utility of plasticizers containing the present liquid ester blends for this application.

To function properly a plasticizer must be compatible with the base polymer. To determine the compatibility of blend C with adhesive polymers, adhesives based on a polyvinyl acetate homopolymer and a vinyl acetate/ethylene copolymer were prepared. The formulations are listed in Table 15, and the adhesives were prepared by stirring the plasticizer into the base emulsions. To test the compatibility of the plasticizer, a six mil-thick film of each adhesive was applied to glass plates using a draw down bar and dried for twenty four hours. All the films were clearer than the base emulsion and free of plasticizer exudation, indicating compatibility at the level of plasticizer tested.

The adhesive performance data are also listed in Table 15.

The emulsion viscosity response, open time, set time and caulk performance data indicate that mixture c of the present invention functions well as an adhesive plasticizer.

TABLE 15

Adhesive Formulations and Performance Data

| Formulation | 1 | 2 | 3 | 4 |
|---|---|---|---|---|
| Ingredient | | | | |
| Vinac(R)XX-230 (Homopolymer) | 100 | 89.5 | | |
| Airflex(R) 300 (Copolymer) | | | 100 | 89.5 |
| Blend C | | 10.5 | | 10.5 |
| Data | | | | |
| Plasticizer compatibility | | | | |
| Vinac(R) XX-230 Dry film appearance, after 24 hours | Very Hazy | Very Slight Haze | Very Hazy | Very Slight Haze |
| Plasticizer viscosity response | | | | |
| Viscosity after 1 hour of preparation (ASTM D-1824) | | | | |
| 2.5 RPM's, Pa · s | 4 | 5.8 | 4 | 19 |
| 20 RPM's, Pa · s | 2.6 | 3.8 | 2 | 10 |
| Viscosity after 24 Hours | | | | |
| 2.5 RPM's, Pa · s | 4 | 5 | 4 | 20 |
| 20 RPM'S, Pa · s | 2.6 | 3.3 | 2 | 11 |
| Set time, seconds | 15 | 10 | 13 | 8 |
| Open time, seconds | <10 | 33 | 8 | 23 |
| Adhesions, Visual rating with 0 = none and 10 = Complete bonding, to paper coated with: | | | | |
| X-300 | 0 | 0 | — | — |
| Nomar(R) 70 | 5 | 9 | — | — |

EXAMPLE 5

Blends of diethylene glycol dibenzoate, triethylene glycol dibenzoate, and a third plasticizer were prepared and tested in the following manner. A glass vial was filled with 10 grams of test material and placed in a freezer at −12° C. for 24 hours. After 24 hours, the vials were examined for signs of crystallization. The results are in Table 16. Samples were rated as a 'Pass' if there were no signs of crystallization.

TABLE 16

| Weight percent in Blend | | | | | |
|---|---|---|---|---|---|
| DOA[1] | DOP[2] | DPGDB[3] | DEGDB[4] | TEGDB[5] | Rating |
| 0 | 0 | 50 | 25 | 25 | pass |
| 0 | 50 | 0 | 25 | 25 | pass |
| 50 | 0 | 0 | 25 | 25 | pass |

[1]DOA is di-2-ethylhexyl phthalate
[2]DOP is di-2-ethylhexyl phthalate.
[3]DPGDB is dipropylene glycol dibenzoate.
[4]DEGDB is diethylene glycol dibenzoate.
[5]TEGDB is triethylene glycol dibenzoate.

The third plasticizer acts as a freeze point depressant for the two solid esters and extends the useful range of the present compositions.

That which is claimed is:

1. A liquid ester composition comprising
   1) a first diester of the formula $ArC(O)(OCH_2CH_2)_2O(O)CAr$ and
   2) a second diester of the formula $ArC(O)(OCH_2CH_2)_3O(O)CAr$;
   wherein Ar represents a phenyl or methylphenyl radical, and the freezing point of said composition is below the freezing points of said first and second diesters.

2. The composition of claim 1 wherein the weight ratio of said first diester to said second diester is from 1.22:1 to 9:1 and Ar represents a phenyl radical.

3. A liquid ester composition comprising
   1) a first diester of the formula $ArC(O)(OCH_2CH_2)_2O(O)CAr$;
   2) a second diester of the formula $ArC(O)(OCH_2CH_2)_3O(O)CAr$; and
   3) at least one additional ester that is a liquid at 25° C.;
   wherein Ar represents a phenyl or methylphenyl radical, the freezing point of said composition is below the freezing points of said first and second diesters and wherein the combined weights of said first and second diesters constitute at least 50 weight percent of said composition.

4. The composition of claim 3 where the weight ratio of said first diester to said second diester is from 0.5:1 to 9:1.

5. The composition of claim 3 wherein said additional ester is at least one member selected from the group consisting of 1) diesters derived from benzoic acid and diols containing from 3 to 10 carbon atoms, 2) esters derived from benzoic acid and monohydric alcohols containing from 4 to 12 carbon atoms, 3) aliphatic esters of the formula $R^1O(O)C(CH_2)_mC(O)OR^1$, wherein each $R^1$ is an alkyl radical individually selected from the group consisting of alkyl radicals containing from 8 to 12 carbon atoms, and m represents an integer from 2 to 8, and 4) esters derived from phthalic acid and alcohols containing from 4 to 12 carbon atoms, wherein the combined weight of additional esters constitutes from 10 to 35 weight percent of said composition and said additional ester is a liquid at 28° C.

6. The composition of claim 5 wherein said additional esters are selected from the group consisting of di(2-ethylhexyl) adipate and di(2-ethylhexyl) phthalate, and dipropylene glycol dibenzoate.

7. An oil composition containing as an additive the liquid composition of claim 1.

8. An oil composition containing as an additive the liquid composition of claim 3.

9. A lubricant composition containing as an additive the liquid composition of claim 1.

10. A lubricant composition containing as an additive the liquid composition of claim 3.

* * * * *